United States Patent [19]
Hansen et al.

[11] Patent Number: 5,876,716
[45] Date of Patent: Mar. 2, 1999

[54] METHOD OF USING AN ANTIBODY TO THE TN ANTIGEN FOR THE INHIBITION OF HIV INFECTION

[75] Inventors: John-Erik Stig Hansen, Frederiksberg C.; Henrik Clausen, Holte, both of Denmark

[73] Assignee: Bay Development Corporation SA, Switzerland

[21] Appl. No.: 368,383

[22] Filed: Dec. 30, 1994

Related U.S. Application Data

[63] Continuation of Ser. No. 46,443, Apr. 12, 1993, abandoned, which is a continuation-in-part of Ser. No. 645,134, Jan. 24, 1991, abandoned.

[51] Int. Cl.$^6$ .......................... A61K 39/42; C07K 16/28; C07K 16/30; C07K 16/10
[52] U.S. Cl. ..................... 424/137.1; 424/148.1; 424/153.1; 424/154.1; 424/155.1; 435/70.21; 435/329; 435/339.1; 435/343.1; 435/343; 435/343.2; 435/344; 435/451; 435/452; 530/388.35; 530/387.5; 530/388.7; 530/388.73; 530/388.75; 530/388.8
[58] Field of Search .......................... 530/388.35, 387.5, 530/388.7, 388.73, 388.75, 388.8; 435/240.27, 172.2, 70.21, 329, 339.1, 343.1, 343, 343.2, 344, 451, 452; 424/137.1, 148.1, 153.1, 154.1, 155.1

[56] References Cited

FOREIGN PATENT DOCUMENTS 8908711  9/1989  WIPO .

OTHER PUBLICATIONS

Zolla–Pazner et al. J. Virol Mtds 17:45–53, 1987.
Fahey et al., Clin Exp. Immunol. 88:1–5 1992.
Hansen et al. J. Virology 64:2833–2840, 1990.
Hansen et al. J. Virology 65:6461–6467, 1991.
Harris et al. Tibtech 11:42–44, 1993.
Kjelcken et al. Cancer Res. 48:2214–2220 1988.
Aguila et al. Immunochemica vol. II (2) pp. 1–4, Jun. 1988.
Cooper, "The Tools of Biochemistry", John Wiley + Sons, 1977, pp. 378–385.

*Primary Examiner*—Anthony C. Caputa
*Attorney, Agent, or Firm*—Ostrolenk, Faber, Gerb & Soffen, LLP

[57] ABSTRACT

A monoclonal or other antibody to the carbohydrate antigen Tn can be used to inhibit or slow the progression of AIDS or ARC. The antigen can be used in a vaccine, for immunisation.

6 Claims, 1 Drawing Sheet

METHOD OF USING AN ANTIBODY TO THE TN ANTIGEN FOR THE INHIBITION OF HIV INFECTION

This is a Continuation of application Ser. No. 08/046,443, filed on Apr. 12, 1993 and now abandoned, which was a continuation-in-part of application Ser. No. 07/645,134, filed Jan. 24, 1991 and now abandoned.

FIELD OF THE INVENTION

The present invention relates to the treatment of acquired immune deficiency syndrome (AIDS) and AIDS-related complex (ARC), and in particular to medicaments for treating AIDS and ARC employing anti-carbohydrate antibodies.

BACKGROUND OF THE INVENTION

Altered glycosylation in host cells associated with viral infection has been reported (Ray et al. (1978) Virology 88:118; Kumarasamy et al. (1985) Arch. Biochem. Biphys. 236:593). Like oncogenesis, aberrant glycosylation induced by cytomegalovirus or by HIV causes formation of new antigens which are absent in the original host cells (Andrews et al. (1989) J. Exp. Med. 169:1347; Adachi et al. (1988) J. Exp. Med. 167:323). Using monoclonal antibodies which define oligosaccharide epitopes, appearance of $Le^y$ and $Le^x$ antigens after viral infection has been detected.

Several studies have indicated the involvement of the carbohydrate part of HIV infection in vitro. Thus, inhibition of the early steps in Golgi glycosylation in infected cells reduces the infectivity of the virus produced (Gruters et al. (1987) Nature 330:74; Montefiori et al. (1988) PNAS 85:9248). Further, lectins block syncytium formation, probably by a specific interaction with gp 120-glycans of infected cells, and also neutralize infectivity of cell-free virus (Lifson et al. (1986) J. Exp. Med. 164:2101). Variation in N-glycosylation of target T4 cells, however, does not seem to influence HIV infection (Montefiori et al. (1988) supra).

Gp120 contains several different glycan structures, and carbohydrate constitutes 50% of the total mass of gp 120 (Matthews et al. (1987) PNAS 84:5424). Predominantly N-linked glycans have been found on gp120 (Kozaraky et al. (1989) J. Acq. Imm. Def. Syndr. 2:163). The binding site on gp120 for the T4 receptor seems to be located in a non-linear C-terminal part of the molecule (Lasky et al. (1987) Cell 50:975). Whether glycans participate directly in virus-binding is not clear. Thus, inhibitory lectins may bind to glycans adjacent to the binding site and thereby sterically interfere with T4-gp120 binding, as has been found for neutralizing antibodies (Bahraoui et al. (1988) AIDS 2:165–169; Linsley et al. (1988) J. Virol. 62:3695). Glycans so far identified on gp120 by lectin studies are ubiquitous, and the therapeutic potential of lectin-based treatment therefore seemed small.

In an article published less than 12 months before the filing date of this Application, the contents of which are incorporated herein by reference, Hansen et al (1990) J. Virol. 64:2833, disclose that three carbohydrate epitopes ($A_1$, $Le^y$, and sialosyl-Tn) were preferentially or exclusively expressed on T lymphoid cells after HIV infection. The simple mucin type structure sialosyl-Tn, as well as the related Tn and T antigens, generally are not expressed at the cell surface of normal adult cells. A humoral immune response directed to these antigens is found in cancer patients, because cancer cells may express these antigens and sensitise the immune system (Springer et al. (1979) Prog. Allergy 26:42). Hansen et al (1990) supra, disclose that antibodies directed to Tn and T did not demonstrate the presence of these antigens on HIV. This was the result of an in vitro immuno-neutralization assay, which is dependent on the special characteristics of the monoclonal antibodies used.

AIDS is recognized as a distinct new disease whose etiology has been identified as being associated with infection of a new class of lymphotrophic retrovirus termed HIV. The disease is characterized by a disorder associated with an impaired cell-mediated immunity and absolute lymphopenia, particularly reduced helper T lymphocytes (T4 or CD4). This is due to the fact that HIV preferentially infects the CD4 lymphocyte population. AIDS may be preceded by ARC, a presyndrome that is usually manifested by a complex of designated clinical features and helper T lymphopenia.

Diagnosis of infection with HIV is usually made on the basis of detecting antibodies directed against HIV. The exact antibody profile may vary with the stage of the disease (Gallo et al. (1986) Prog. Allergy 37:1).

Despite the significant advances that have been made to characterize them, methods of treating and preventing AIDS and ARC are still poorly developed. A great need exists to develop better methods for their treatment and prevention.

SUMMARY OF THE INVENTION

A novel antibody is anti-Tn. A monoclonal antibody of this type can inhibit in vitro HIV infectivity and syncytium formation, either by binding to the virus or to the target cells used. It can therefore also be used to define carbohydrate structures expressed as viral glycoproteins and glycosphingolipids associated with the virus, thereby identifying glycans of the viral capsule as targets that are expected to be useful for immuno-therapy and/or vaccine development.

The novel antibody may be used to inhibit or slow the progression of AIDS or ARC. A medicament for this purpose comprises a pharmaceutically-effective amount of one or more antibodies consisting of anti-Tn, and a pharmaceutically-acceptable carrier, diluent or excipient.

In another embodiment, the present invention provides a vaccine against AIDS and ARC comprising an immunologically-effective amount of one or more Tn antigens, and a pharmaceutically-acceptable carrier, diluent or excipient. A method of actively immunizing against AIDS and ARC comprises administering to a subject a medicament comprising an immunologically-effective amount of one or more Tn antigens, and a pharmaceutically-acceptable carrier, diluent or excipient.

DETAILED DESCRIPTION OF THE INVENTION

Figure 1:
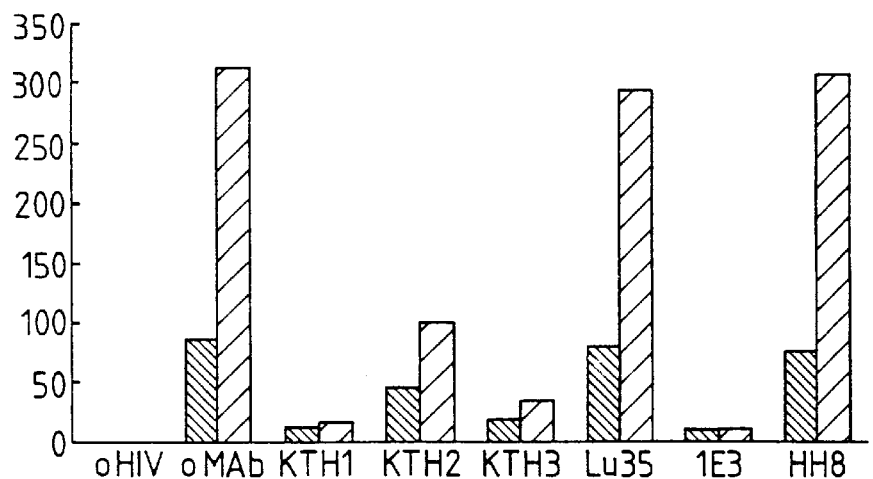
FIG. 1 is a bar graph showing the inhibitory effects of various monoclonal antibodies on HIV infection of cells. The ordinate represents antigen production, in arbitrary units, and the abscissa represents control with untreated virus ("No MAb"), control without virus ("No HIV"), or hybridoma supernatant containing the designated monoclonal antibodies (MAb).

Carbohydrate structures are often involved in initial adhesion of pathogens to target cells. In developing the present invention, a panel of anti-carbohydrate monoclonal antibodies was tested for their ability to inhibit in vitro HIV infectivity, either by binding to the virus or the target cells used. Monoclonal antibodies to the carbohydrate antigen were able to block infection by virus as well as to inhibit syncytium formation. The inhibition of virus infectivity was independent of virus strain (HTLV$_{III}$B and a patient isolate SSI-002), cell line used for virus propagation (H9 and MT4) or cell type used as infection target (lymphocytes or monocytes). Inhibition was observed when monoclonal antibodies were preincubated with virus, but not when cells were so preincubated before infection. The monoclonal antibodies thus are believed to define carbohydrate structure expressed as viral glycoproteins, and glycans of the viral envelope are expected to be useful targets for immunotherapy and/or vaccine development.

The anti-Tn antibody should be specific for the Tn carbohydrate antigen having the following structure:

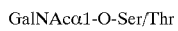

GalNAcα1-O-Ser/Thr

The anti-Tn MAb may cross-react with the sialosyl-Tn carbohydrate antigen having the following structure:

NeuAcα2-6GalNAcα1-O-Ser/Thr

The isotypes and affinities of suitable anti-Tn antibodies for the antigen vary extensively from one antibody to the next, and thus the specificity to Tn is the critical identifying characteristic of these antibodies.

Examples of preferred murine monoclonal antibodies include those produced by the novel hybridomas KTH1, KTH2 and KTH3, all deposited on 14th Nov. 1990 at the PHLS Centre for Applied Microbiology and Research, European Collection of Animal Cell Cultures, Porton Down, Salisbury, Wiltshire, England. The three respective deposits have the accession Nos. 90111401, 90111402 and 90111403. However, any other monoclonal antibodies having the identifying characteristics of monoclonal antibodies KTH1, KTH2 and KTH3 may be used.

In addition to binding specifically to the carbohydrate antigen Tn, a further identifying characteristic of monoclonal antibodies KTH1, KTH2, and KTH3 is their isotypes which are IgG$_1$, IgM and IgM, respectively.

Polyclonal antibodies to the carbohydrate antigen Tn may be prepared by known methods.

The immunogen used to obtain the antibody to Tn antigen is a core structure of many mucin-type glycoproteins. "Mucin-type glycoprotein", as used herein, means a high molecular weight protein with a high degree of o-linked glycosylation at serine or threonine residues. Mucin-type glycoproteins are further polymerized by S—S dependent linkage and are the major components of epithelial secretions. "Core structure of mucin-type glycoprotein", as used herein, means a basic carbohydrate structure without peripheral substitution and which is directly linked to the protein moiety of a mucin-type glycoprotein. In the present invention, any Tn core structure of a mucin-type glycoprotein can be used as an immunogen as long as the glycoprotein has a high molecular weight (relative molecular weight>$10^6$ daltons) and is glycosylated to the same degree as mucin, i.e., more than 50% of total weight is glycosylated. Animal mucins containing the Tn antigen can also be used as an immunogen.

The Tn antigen immunogen can be obtained by enzymatic or chemical modification of a mucin-type glycoprotein to expose the Tn antigen core structure or by isolation of mucins having on them Tn core structures. These mucins are present in some animal species. The Tn antigen immunogen can be isolated and purified according to conventional methods.

By way of example, mucin-type glycoproteins which will be enzymatically or chemically modified to produce a sialyl-Tn core structure can be isolated by gel filtration through Sepharose 4B or Sephacryl 200S. The isolated glycoprotein is then enzymatically or chemically modified, by methods described below, to expose the Tn core structure, and the Tn core structure is purified for use as an immunogen.

For purification, the modified mucin can be separated by gel filtration, e.g. through Sepharose 4B or Sephacryl 200. High pressure chromatography on a synthetic molecular filter column (fast liquid chromatography; Pharmacia) is also useful to separate enzymatically- or chemically-modified mucins. However, as an immunogen for making monoclonal antibodies, the modified mucin does not need to be purified. The presence of a small quantity of unmodified mucin will not be harmful for use as an immunogen for the purposes of the present invention. Further, modification is usually quantitative, if appropriate routine precautions are taken.

Mucins which are derived from animal species and contain glycoproteins already in the form of a sialyl-Tn core structure are obtained by conventional methods, e.g. by gel filtration through Sepharose 4B, Sephacryl 200, or FPLC, as described above.

Examples of types of enzymatic modifications that can be used to expose the Tn structure of various mucin-type glycoproteins include the elimination of the terminally-located α2-3 sialyl residue and α2-6 sialyl residue attached to the GalNAc by specific sialidases or the total elimination of all sialic acid residues by *Clostridium perfringens* sialidase. Enzymatic modification can also include treatment with β-galactosidase (preferably from *Charonia lampas*), α-fucosidase, and N-acetylhexosaminidase. Enzymatic hydrolysis of mucin glyprotein is described by Hirohashi et al (1985) PNAS 82: 7039–7043, and Kjeldsen et al (1988) Cancer Res. 48: 2214.

Examples of chemical reactions which can be used to expose the Tn core structure of mucin-type glycoproteins include periodate oxidation followed by reduction with sodium borohydride and treatment with weak acid. The procedure is called Smith degradation (Sprio, Methods Enzymol. (1972) 28: 3–43). This chemical treatment eliminates non-reducing terminals of carbohydrate residues, except sialic acid which can be eliminated by sialidase treatment, as described above.

Examples of mucins isolated from animals that can be used as immunogens include ovine submaxillary mucin (OSM) in which 90% of the carbohydrate chains consist of the Tn antigen and bovine submaxillary mucin (BSM) in which 50% of the carbohydrate chains consist of the Tn antigen and 20% of the carbohydrate chains consist of T antigen and other unidentified residues. The Tn-antigen is produced from the sialosyl-Tn mucins by elimination of sialosyl residues using sialidases.

This thus-derived animal mucins can be further purified for use as immunogens by the same methods, such as conventional gel filtration or FPLC as described above. However, the purity of the immunogen is not critical for the production of a monoclonal antibody.

Human erythrocyte glycophorin can be obtained from human erythrocyte membranes by the method originally described by Marchesi and Andrews, Science (1971) 174: 1247–1248.

Whether a glycoprotein has the Tn core structure can be determined by affinity chromatography with a *Helix pomatia* column (Carter and Sharon (1977) Arch. Biochem. Biophys. 180: 570–582), or by immunoblotting of glycoproteins with anti-Tn antibody (available from Chembuimed, Edmonton, Alberta, Canada).

The distribution of the antigen is rather limited. However, one source of the Tn antigen which is useful in the present invention is culture supernatants of squamous lung carcinoma cell lines QG 56 and LU-65 (Hirohashi et al (1985) supra, and Takahashi et al (1988) Cancer Res. 48: 4361).

A second source is again ovine submaxillary mucin, which contains a high density of sialyl-Tn which may be chemically or enzymatically converted to Tn.

A third source is a biosynthetically-produced Tn-protein. Synthetic peptides or recombinant proteins containing serine and/or threonine amino-acid residues may be glycosylated in vitro with a naturally-occurring glycosyltransferase (UDP-GalNAc: Serine/Threonine-peptide N-acetylgalactosaminyltransferase); see Elhammer et al (1982) J. Biol. Chem.

A fourth source is chemically-synthesized GalNac α1-0-Ser or GalNAc α1-0-Thr (commercially available from Biocarb, Sweden).

In order to obtain Tn antigen in a form useful as the immunogen for the purpose of the present invention, from culture supernatant, the various cell lines described above are cultured according to known methods. The culture supernatants are then treated to obtain sialyl-Tn antigen as follows.

For example, the treatment is as follows: the spent culture medium from cells cultured in suspension is lyophilized to reduce its volume to 1/50 of the original volume. The concentrated spent medium is then dialysed extensively against phosphate-buffered saline containing 0.01% sodium azide at 4° C. The dialysed material is placed on Sepharose 4B and gel-filtered. The void volume is pooled, concentrated further, and re-chromatographed on Sephacryl 200. The glycoprotein fraction in the void volume is used as immunogen. All procedures must be completed within a limited time and at low temperature (4° C.), since the sialyl linkage is unstable.

The immunogen can then be treated for immunization. For example, the Tn antigen (e.g. 4.0 mg) is dissolved in distilled water (e.g. 4 ml), thoroughly mixed with an appropriate amount of acid-treated *Salmonella minnesota* (e.g. 16 mg), and lyophilized. The dried mixture is suspended in a suitable volume (e.g. 4.0 ml) of an appropriate carrier (e.g. 140 mM NaCl containing 20 mM phosphate buffer, pH 7.0), and aliquots of about 100 μg of mucin and 400 μg of bacteria are injected intravenously.

Immunization can also be made with complete Freund's adjuvant instead of absorption on bacteria, and the ratio between the amount of mucin and *Salmonella minnesota* can be varied. The best results have been observed when *Salmonella minnesota* is treated with acetic acid, as previously described by Young et al. (1979) J. Exp. Med. 150:1008–1019.

The host used for immunization can be a mouse or rat of any strain or any other type of animal whose splenocytes are suitable for preparation of hybridomas, i.e., susceptible to cell fusion with HAT-sensitive myeloma cell lines, to establish stable hybridomas.

The immunization schedule depends upon the host animal susceptibility to mucin immunization, but the protocol described above is suitable for mice. Alternative conditions can also be applied. Suitable immunization schedules can be determined by the skilled artisan.

For example, a suitable immunization schedule for Balb/c mice is to inject the immunogen preparation intravenously through the caudal vein once a week for 5 weeks and then, after a one-month intermission, to boost with the immunogen preparation.

The amount of immunogen preparation administered to the host depends upon the molecular weight of the mucin, the exposure of the carbohydrate epitope, and the novelty and density of the epitope associated with mucin-type glycoproteins. The range of glycoprotein injected in mice is 3–5 μg coated in 100 μl of saline, intravenously injected in each individual mouse, whose body weight range is 100–150 g.

When complete Freund's adjuvant is used, about 20 μl of glycoprotein in 500 μl of saline is emulsified with 500 μl of complete Freund's adjuvant and about 200 μl is injected subcutaneously at multiple sites (about 50 μl per site).

Similar quantities of antigen, either coated on *Salmonella minnesota* or mixed with complete Freund's adjuvant, are used for other hosts such as rats, hamsters, or guinea pigs, and several times greater quantities are used for other hosts such as rabbits. It is not necessary to increase the amount of antigen in proportion to the body weight of the animal.

Immunization is repeated until sufficient antibody is detectable in whole serum. The spleen cells of the host are removed and splenocytes are fused with HAT-sensitive myeloma cells by the technique that has been well-established (Köhler and Milstein (1975) Nature 256:495–497, and Young et al (1979) supra).

HAT-sensitive myeloma cells can be NS-1, SP-1 or (preferably) SP-2, foi example, but any type of HAT-sensitive myeloma cells can be used. Occasionally, hybridomas can be established after fusion of host splencytes with myeloma cells, even though no antibody was detectable in the host serum. Therefore, it is not essential to detect antibodies before cell fusion. Fusions are usually carried out in polyethylene glycol, as described by Young et al (1979) supra).

The fused cells are cultured in 96-well plates until mini-clones are formed. It is important to use splenocytes 48–72 hours after the last booster injection and to fuse with well-proliferating myeloma cells, to obtain a number of surviving fused cells that will grow. Moisture and $CO_2$ concentration in the incubator must be carefully controlled at the initial stage of culturing the fused cells.

One skilled in the art can readily determine suitable culture conditions. Feeder cells are not necessary to grow the fused cells according to the process of the present invention.

After an appropriate culture period, hybridomas secreting antibodies that react with the sialyl-Tn antigen that was used to immunize are cloned and subcloned by limiting dilution, i.e., by diluting to a point where less than one cell per new culture will be expected, and then plating into the wells.

In general, each well of a 96-well plate is coated with mucin glycoprotein containing the Tn core structure used as immunogen, by incubation of each well with glycoprotein solution in PBS, e.g. 100 μl of 0.1–10 μg/ml of solution is added and incubated overnight. Glycoprotein solution is removed, washed, and further incubated with 5% bovine serum albumin, to block the plate before using it to screen antibodies. This method is described by Hirohashi et al (1985) supra.

The hybridomas that secrete the antibodies that react with the particular antigens are screened as follows: Antibody bound to an antigen-coated well is usually detected by secondary antibody (anti-mouse IgM and IgG goat or rabbit antibodies) followed by $^{125}$I-labelled protein A as initially described by Young et al (1979) supra. The method is still more sensitive than available ELISA assays, although an ELISA can also be used. ELISA's can be more conveniently processed by use of automated readers and ELISA kits available commercially.

Monoclonal antibodies to Tn antigen secreted by hybridomas thus isolated can be produced in quantity by growing large batches of hybridoma cell cultures and purifying the antibody from the supernatant or by injecting mice with the hybridoma line to stimulate the production of ascites fluid. Both methods are well known in the art.

Methods of producing the monoclonal antibody in quantity according to the present invention are described by Young et al (1979) supra.

The hybridomas isolated according to the present invention can be grown in large batches in suspension culture, or more conveniently in a fibreglass container in which cells are packed and grown in high density, wherein antibodies can diffuse into the culture medium.

The monoclonal antibodies can be purified by known methods, for example, by affinity separation using protein A or high-pressure liquid chromatography on reverse-phase alkylated silica gel, or using a synthetic polystyrene gel filtration column.

Suitable doses of medicament can readily be determined by the skilled artisan, depending upon the mode of administration. More specifically, a suitable dosage for intravenous administration of antibodies to suppress further AIDS infectivity should be determined by various conventional experiments. For example, KTH1, KTH2 and KTH3 antibodies can inhibit HIV infection at 2 μg/ml concentration in vitro. 15.6 mg of KTH-1 is believed sufficient to prevent HIV infectivity when administered to a man of 60 kg weight who has approximately 7.8 l of blood. Humanized antibodies are highly preferable, to perform this in vivo inhibition.

Suitable methods of administration of the medicament can be determined by those skilled in the art. Antibodies can be administered intravenously, but other forms of administration are also possible.

Suitable pharmaceutically-acceptable carriers, diluents and excipients are readily determined by the skilled artisan. For example, the antibodies can be administered when solubilized in a physiological buffer solution. However, no carrier is considered especially preferable.

The antigen Tn, whose structure is set forth above, can be isolated from natural sources by known methods, such as that described by Kjeldsen et al (1988) Cancer Res. 48: 2214, or by the method described above for preparing purified immunogen comprising the Tn antigen or biosynthetically produced Tn-glycopeptide.

Suitable methods of administration, immunologically-effective doses and pharmaceutically acceptable carriers, diluents and excipients for a vaccine of the invention can readily be determined by the skilled artisan. For example, an immunologically-active dose of Tn antigen as a vaccine will be approximately 55 μg per injection. However, the carrier molecule is important: BCG coated with Tn antigen is considered to be a useful way to prevent AIDS infectivity. One example is 50 μg of Tn antigen coated on 500 μg of BCG to be injected intradermally or subcutaneously.

The following Examples illustrate how antibodies of the invention may be prepared, and the tests illustrate their utility. Unless otherwise specified, all percentages, ratios, parts, etc. are by weight. FCS=Foetal Calf Serum.

Anti-carbohydrate monoclonal antibodies

Antibodies tested, their specificity, isotype, and reference for production, are listed in Table 1. The different monoclonal antibodies shown in Table 1 define carbohydrate structures found at the periphery of O-linked chains of glycoproteins (for a review, see Clausen and Hakomori (1989) Vox Sang. 56:1).

All cells were grown in RPMI 1640 containing 5–15% FCS 2 mM glutamine and 1 mM pyruvate, and stored at 4° C. with 0.02% NaN$_3$.

Initially, all listed monoclonal antibodies were tested for HIV-inhibition as sterile culture hybridoma supernatants containing about 10–50 μg immunoglobulin (Ig)/ml.

Figure 2:
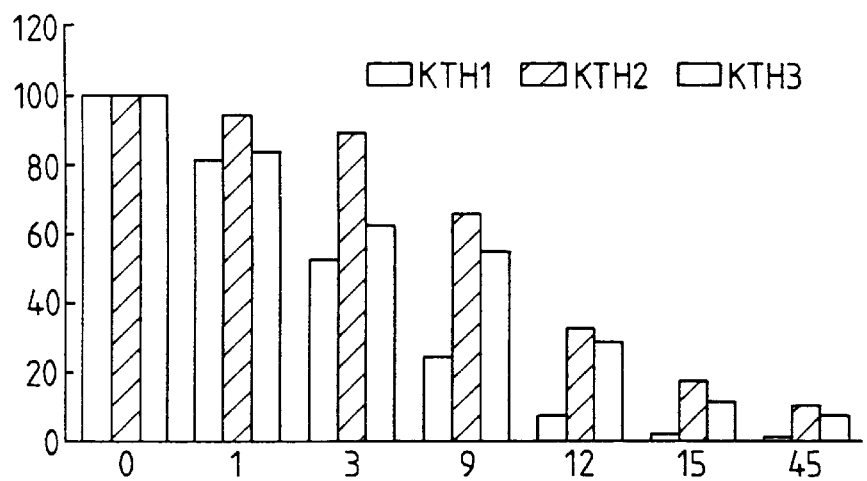
FIG. 2 is a bar graph showing inhibitory dose-response relation between concentration of three anti-Tn MAbs and HIV infection of lymphocytes. The ordinate represents HIV antigen production after four days of culture as percent of mock-treated controls, and the abscissa represents the concentration of MAb relative to viral innoculum (namogram per 50% cell culture infectious dose).
Figure 3:
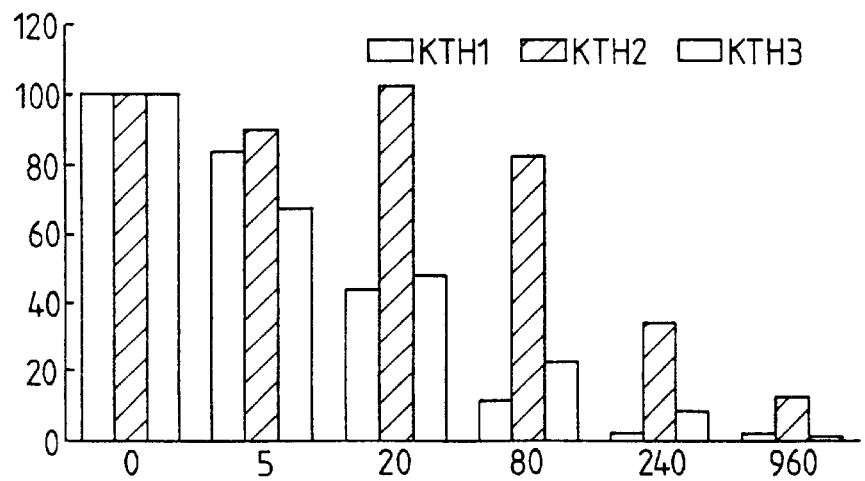
FIG. 3 is a bar graph showing inhibitory dose-response relation between concentration of three anti-Tn MAbs and HIV infection of monocytes. The ordinate represents HIV antigen production after ten days of culture as percent of mock-treated controls, and the abscissa represents the concentration of MAb relative to viral innoculum (nanogram per 50% cell culture infectious dose).

Finally, the monoclonal antibodies KTH1, KTH2 and KTH3 were used after purification from culture supernatant (see below; FIGS. 2 and 3). KTH1 (IgG$_1$) was purified by protein A-Sepharose chromatography, and KTH2 (IgM) and KTH3 (IgM) by ion-exchange chromatography as described by the manufacturer (Pharmacia, Uppsala, Sweden).

The articles to which Table 1 refers are:

1) Hirohashi (1985) PNAS 82: 7039
2) Clausen et al, unpublished
3) Clausen et al (1988) Molec. Immunol. 25:199
4) Kjeldsen et al (1988) Cancer Res. 48:22

TABLE 1

| | Antigen | Antibody | Ref. |
|---|---|---|---|
| Tn | GalNAcα1-O-Ser/Thr | KTH1 (IgG) | |
| | | KTH2 (IgM) | |
| | | KTH3 (IgG) | |
| | | Lu35 (IgM) | 1) |
| | | 1E3 (IgG2A) | 2) |
| Sialosyl-Tn | NeuAcα2-6GalNAcα1-O-Ser/Thr | KTH3 (IgM) | |
| | | TKH2 (IgGl) | 4) |
| | | B72.3 (IgGl) | 4) |
| T | Galβ1-3GalNAc α1-O-Ser/Thr | HH8 (IgM) | 3) |

Cells

For HIV infection experiments, the T4-lymphocyte cell lines H9 (Popovic et al (1984) Science 224:497), CEM (Foley et al (1965) Cancer 18:522) and MT4 (Harada et al (1985) Science 229:563) were cultured at 37° C., 5% CO$_2$ using RPMI 1640 with 10% FCS (5% for CEM cells), 100 IU/ml penicillin, 20 μg/ml gentamicin and 100 IU/ml streptomycin (growth medium). Cells were maintained at a concentration of 2–10×10$^5$ cells/ml, and medium was exchanged twice weekly.

For HIV infection experiments in monocytes, the cell line U937 (Levy et al (1985) Virology 147:441) was used after culture as described above.

Virus Source

Supernatant from H9 cells chronically infected with reference HIV-1 strain HTLV$_{III}$B (Popovic et al (1984) Science 224:497) was sterile-filtered, aliquotted and stored at −80° C. until use. HIV-1 strain SSI-002 was isolated from an HIV-infected patient (CDC II) as previously described (Nara et al (1989) PNAS 86:7139–43). The virus was then passed three times in MT4 cells, and stored as above. Before use, the TCID$_{50}$ of the virus preparations was determined in MT4 cells and U937 cells.

Toxicity

Toxicity of the monoclonal antibody preparations was examined by incubating $0.5 \times 10^6$ MT4 cells in 24-well cell culture plates in growth medium containing from 20 to 0 μg/ml purified antibody, and supernatants were exchanged with fresh medium containing appropriate concentrations of antibody after 4 days of culture. Live cell counts were obtained on days 0, 4 and 7 using trypan blue exclusion.

ELISA

Cell-free supernatants were examined for HIV antigen using a double-antibody sandwich ELISA; see Nielsen et al (1987) Lancet 8532:566. Each plate included a dilution series of a standard HIV antigen preparation, and optical densities (490 nm) were expressed relative to this standard preparation (arbitrary units). All in vitro infection experiments included a control using untreated HTLV$_{III}$B. After 4 days in culture, supernatants were diluted to give an OD490 from this control of approximately 2. All antibodies tested for inhibition of infection were also tested for interference wit the ELISA detection, and no such interference was found.

Screening

The newly-developed hybridoma supernatants containing monoclonal antibodies stimulated by immunisation with Tn, i.e. KTH1–3, were screened both by antigen specificity using Tn antigen, as well as in the virus inhibition assay as described below. Established control antibodies included anti-Tn antibody Lu35 previously found to be non-inhibitory (Hansen et al (1990) supra) and IgG2A anti-Tn monoclonal antibody 1E3 (Clausen et al unpublished). In addition, antibodies previously found to be inhibitory directed against sialosyl-Tn antigen. TKH2 and B72.3 (Kjeldsen et al (1988) supra) were included as positive controls. An anti-T antibody, HH8 (Clausen et al supra), was also include as a negative control (see Table 1).

Virus inhibition assay

Twenty-five TCID$_{50}$ HTLV$_{III}$B was mixed with 0.5 ml hybridoma supernatant and incubated for 1 hour at 37° C. MT4 cells ($1 \times 10^6$) were suspended in this mixture and incubated for 2 hours at 37° C. After extensive washing, the cells were resuspended in growth medium (4 ml) containing 10% v/v of the corresponding MAb.

Results are shown in FIG. 1. In FIG. 1, the ordinate represents antigen production, in arbitrary units, after 4 days (solid column) and after 7 days (hatched); the abscissa represents control with untreated virus ("o MAb"), control without virus ("o HIV"), or hybridoma supernatant containing the designated Mab.

Infection Inhibition

In order to determine the inhibitory effect of the MAbs on HIV infection in different cell systems, lymphocytic cells of the MT4 cell line and monocytic cells of the U937 cell line were used as target cells for infection with the HIV-1 virus strains HTLV$_{III}$B or SSI-002 respectively.

$10^6$ MT4 cells in 500 μl growth medium were inoculated with 25 CCID$_{50}$ HIV-1 for 2 hours. Prior to inoculation, either the cells or the viral inoculum were preincubated for 1 hour with a dilution series of MAb. MAb-preincubated cells were washed before inoculation. After inoculation, cells were washed and quadruplicates of 200,000 cells were cultured in growth medium without MAb in 24-well NUNC-dishes for 7 days. After 4 days of culture, HIV antigen in the culture medium was measured using a double-sandwich ELISA (Hansen et al (1990) supra). Antigen concentration was expressed relative to antigen concentration at corresponding days in control-cultures of mock-treated cells inoculated with mock-treated HIV. Inhibition of infection in U937 cells was assayed in a similar manner: $2 \times 10^6$ U937 cells were inoculated with 25 CCID$_{50}$ SSI-002 and subsequently cultured in quadruplicate for 2 weeks. Infection of U937 cultures was evaluated at day 10.

The results are shown in FIGS. 2 and 3. In FIG. 2, the ordinate represents HIV antigen production (% of control) 4 days after infection of MT4 cells with HTLV$_{III}$B treated with MAb. In FIG. 3, the ordinate represents HIV antigen production (% of control) 10 days after infection of U937 cells with HIV-1 isolate SSI-002 treated with MAb. In each of FIGS. 2 and 3, the abscissa reapresents the concentration of MAb relative to virus inoculum (nanogram per 50% cell culture infectious dose).

FIGS. 2 and 3 show that purified MAb KTH1–3 effected a concentration-dependent inhibition of HIV infection in lymphocytic as well as in monocytic cells using two different strains of HIV-1. The 80% effective doses of the MAbs KTH1–3 in the lymphocytic and monocytic cell systems respectively were 10–15 and 40–500 ng per 50% cell culture infectious dose.

Specificity of Inhibition

Infectivity assay was performed as above after preincubation of either virus or cells with MAb or after preincubation of virus or cells with MAb plus sythetically produced Tn-antigen, GalNAc-Ser (BioCarb, Lund, Sweden).

Either MT-4 cells or HTL$_{III}$B were preincubated with 20 and 4 nanogram MAb KTH1 per CCID$_{50}$ or PBS. Before inoculation with 25 CCID$_{50}$ HTLV$_{III}$B, preincubated cells were washed thoroughly. Infection at day 4 was expressed as HIV antigen concentration in culture supernatants relative to a mock-treated control culture (percent). Results are shown in Table 2 as the mean of quadruplicate determinations.

TABLE 2

| | Preincubation of | |
|---|---|---|
| | HIV | Cells |
| 4 ng KTH1/CCID$_{50}$ | 45.6% | 99.1% |
| 20 ng KTH1/CCID$_{50}$ | 1.7% | 105.2% |
| 100 μg GalNAc-Ser | 100.4% | 97.3% |
| 4 ng KTH1/CCID$_{50}$ + 100 μg GalNAc-Ser | 97.8% | 98% |

Table 2 shows that inhibition of HIV infection by anti-Tn antibody (MAb KTH1) was a result of antibody-binding to virus not to cells. The inhibition of infection was abrogated by GalNAc-Ser (Tn-antigen). This confirms that the inhibition of infection was a result of a specific interaction of MAb with virus.

Inhibition of Syncytium Formation

HTLV$_{III}$B-infected H9 cells ($2 \times 10^4$) were preincubated for 1 hour in 50 μl growth medium containing 0, 5 or 50 ng KTH1 in a well of a 96-well cell culture plate. The $10^5$ CEM cells in 50 μl growth medium were added. After coculture for 24 hours, the total number of syncytia (multi-nucleated giant cells with "ballooning" cytoplasm) was counted by microscopy.

Results showing the reduction of syncytial activity of HIV-infected and non-infected lymphocytes, by anti-Tn MAb KTH1, are given in Table 3.

TABLE 3

| KTH1 (ng) | Syncytia per well |
|---|---|
| 0 | 36 |
| 5 | 19 |
| 50 | 4 |

The results indicate that Tn-antigens may be expected to function as targets for passive immunotherapy using anti-Tn antibodies.

Two MAbs of this invention, i.e. KTH1 (IgG) and KTH2 (IgM) are specific to the Tn antigen, while MAb KTH3 (IgM) is an antibody against the Tn antigen and the sialosyl-Tn antigen. For immunization purposes, however, sialylated Tn (NeuAc$\alpha$2→6GalNAc$\alpha$1→O-Ser/Thr) is much more difficult to prepare synthetically that the immediate precursor, Tn (GalNAc$\alpha$1→-O-Ser/Thr). All three MAbs were found to inhibit HIV infection in vitro. The inhibition was demonstrated to be concentration-dependent and was a result of an epitope-specific (GalNAc-Serine) interaction with virus and not with uninfected cells. Anti-Tn MAb was also found to inhibit syncytium formation between infected and uninfected cells.

Antibody-mediated inhibition of HIV has recently been confounded by observations that some antibodies may enhance infection of monocytes/macrophages (Matsuda et al (1989) Scand. J. Immunol. 30:425; Robinson et al (1989) PNAS 86:4710). However, it has been found that the anti-Tn antibodies employed in this invention not only inhibited infection of lymphocytes (MT4 cells) but also inhibited infection of monocytes (U937 cells).

HIV-neutralizing antibodies are found in HIV-infected patients and have also been produced in vitro using selected synthetic peptides from gp120 and gp41 (Weber et al (1989) Lancet i:119; Chanh et al (1986) EMBO J. 5:3065; Lasky et al (1986) Science 233:209). These do not seem to protect against disease progression and are type-specific. "Escape" mutants of HIV, containing mutations in the env gene, have been shown to arise in vitro, whereby the virus is able to escape the effect of formerly neutralizing antibodies (Weiss (1988) J. Acq. Imm. Def. Syn. 1:536).

The anti-HIV reactivity of antisera against Equine infectious anemia virus is described against a carbohydrate part of the HIV envelope (Montelaro et al (1988) J. Gen Virol. 69:1711), but HIV-neutralization by carbohydrate-specific antibodies has not previously been described. Carbohydrate epitopes may not be expected to be influenced as readily by mutations in the genome coding for the peptide part of the HIV envelope. Thus, the present results indicate that viral glycans can be considered targets for anti-viral immunotherapy and/or vaccine development.

EXAMPLE 1

Anti-Tn MAbs and Hybridomas
Isolation of Immunogen
Sialidase-treated ovine submaxillary mucin (OSM) was used as the source of the Tn antigen. Approximately 90% of the carbohydrate chain on OSM consists of the sialyl-Tn antigen, which after sialidase treatment is converted to Tn-antigen.

OSM was isolated from ovine sumaxillary glands by conventional methods (Tettamanti and Pigman (1968) Arch. Biochem. Biophys. 124:45–50). Briefly, an aqueous extract of submaxillary glands was precipitated at acidic pH (e.g. 3.5). This is called a mucin clot. The mucin clot was centrifuged and dissolved in water, the pH was adjusted to neutral, and fractional ethanol precipitation in sodium acetate was performed.

Immunization and establishment of monoclonal antibodies
The higher molecular weight Tn antigen isolated as described above was dissolved in distilled water in an amount of 1.0 mg protein/4 ml water, and mixed with equal volumes of Freund's complete and incomplete adjuvants. The mixture was thoroughly mixed for 1 hour at 37° C.

Aliquots of 200 $\mu$l (i.e. 200 $\mu$g of the glycoprotein and 400 $\mu$g of bacteria) were injected intraperitonously into Balb/c mice. A first injection with Freund's complete adjuvant was followed two weeks later by an injection of Freund's incomplete adjuvant. A final boost was given intravenously without adjuvant (100 $\mu$g in 200 $\mu$l saline).

Three days after the booster injection, the animals were sacrificed, the spleen cells were removed, and splenocytes were fused with mouse myeloma NS-1 cells by conventional methods (Köhler et al, supra).

Hybridomas which grew on selective media were screened by conventional methods for monoclonal antibody reactivity with the OSM described above, desialyated OSM, and glycophorim A. Glycophorin A was purchased from Sigma Chemical Company, St. Louis, Mo.

OSM was desialylated by treatment with 0.1 unit/ml of neuraminidase from *Clostridium perfringens* Type X (Sigma) by conventional methods (Kjeldsen et al (1988) supra).

Approximately 40 hybridomas were found which secreted monoclonal antibody that gave a positive reaction with desialylated-OSM. Of these, 32 also reacted with OSM. Cross-reaction between desialylated OSM (Tn antigen) and OSM (sialosyl-Tn) was found to be a predominant phenomenon of the mouse (as well as the rabbit, see below) immune response to immunization with Tn antigen (desialylated OSM). Nearly all hybridomas binding exclusively desialylated OSM or cross-reacting with OSM were able to neutralize HIV in vitro infection in the standard assay as described in detail by Hansen et al (1990) supra. In addition, the Tn antigen specificity of the MAbs was confirmed by immunofluorescence histology on various section with known Tn and sialosyl-Tn antigen distribution (Hirohashi et al (1985) supra). These hybridomas were scaled up, and the reactivity of the monoclonal antibodies was reexamined with OSM, desialylated OSM, and glycophorin A. Hybridomas secreting monoclonal antibodies showing strong reactivity with desialylated OSM and no reactivity with glycophorin A or OSM were found, as well as antibodies showing reactivity with both OSM and desialylated OSM.

In initial studies, the source of antigen has been ovine mucins carrying 90% Tn as main antigenic epitope. Mucins are not only large glycoproteins, but also difficult to purify to homogeneity and to obtain structural information about. In addition, the ovine origin introduces problems related to use in human vaccines. It is in order to eliminate these obstacles that a semi-biosynthetic approach to the production of these antigens has been developed, as described in the following Example.

EXAMPLE 2

Biosynthetic Tn-antigen
Peptide Synthesis
Naturally-occurring amino-acid sequences, of up to approx. 40 amino-acid residues, may be synthesised from the constituent amino-acids by standard methods. In this Example, sequences of OSM protein core or that of the GP120 HIV envelope protein have been used. In order to be able to immobilise the synthesised peptide reversibly, we have chosen to include a $N_2$-terminal cysteine residue with a SH-reactive group through which the peptide may be reversible coupled to, e.g. TNB-Thiol agarose (Pierce, Ill., USA). The peptide in this case contains Ser and Thr.

Solubilisation and isolation of UDP-GalNAc: polypeptide α-N-acetylgalactosaminyl transferase A suitable source of the transferase is bovine colostrum or bovine thymus, but this transferase is present in many animal and human tissues as well as cell lines (Elhammer et al (1986) J. Biol. Chem. 260: 5249). The transferase may be solubilised with Triton X-100 and purified by affinity chromatography on deglycosylated-OSM-Sepharose as described by Elhammer et al (1982), supra. Alternatively, it has been found that, e.g. Cibacron blue agarose (Sigma Chemicals) binds the enzyme solubilised from bovine thymus, and the transferase may be eluted by KCl. In addition, the transferase may be bound to a serine/threonine-containing synthetic peptide coupled through a N-terminal cysteine residue to TNB-thiol agarose, and eluted with EDTA and salts or UDP. Purification of the transferase, and amino-acid sequencing, will allow cDNA cloning of the transferase gene, with the consequent possibility of using recombinant transferase protein. In addition, cloning of the gene will allow transfection and expression of the transferase in a cell, making it possible to design glycosylation of other recombinant proteins expressed by transfection of CDNA.

Glycosylation of synthetic peptide containing serine/threonine residues

The immobilised peptide (TNB-thiol agarose) may be glycosylated by the addition of α-N-acetylgalactosamine from UDP-GalNAc, catalysed by the UDP-GalNAc: polypeptide α-N-acetylgalactosaminyl transferase in the presence of $MnCl_2$. For present purposes, the transferase may be purified to homogeneity or used in a less pure state. By incubating the peptide-agarose with the transferase and UDP-GalNAc, approx. 80% of serine and threonine residues are glycosylated as evidenced by incorporation of $[^{14}C]$ GalNAc. After glycosylation, the agarose may be washed extensively, and the glycopeptide formed may be released by reducing agents (2-mercaptoethanol or DTT): the glycopeptide is obtained in homogeneous form, and may be subjected to structural confirmation analysis, as is easily determined by the skilled artisan.

Production of biosynthetic Tn-immunogen

The Tn-glycopeptide produced may be coupled to a suitable carrier protein by using the SH-reactive group of a potential $N_2$-terminal cysteine group, as described, e.g. by Pierce, Ill., USA, using maleimide-activated keyhole Limpet Hemocyanin or by any other available method easily determined by the skilled artisan.

Conclusion

Carbohydrate epitopes associated with the HIV evelope protein GP120 have been identified, which are not normally expressed in the human organism. Monoclonal antibodies directed to these carbohydrate epitopes neutralise in vitro HIV infection as well as syncytium formation, suggesting that a vaccine could be based at least partly on carbohydrates expressed by HIV. Preliminary vaccine studies in rabbits using these carbohydrates support this idea.

While studies originally identified three carbohydrate epitopes (histo-blood group A, $Le^Y$, and sialosyl-Tn), data now suggest that the carbohydrate antigen Tn is an equivalent or better immuno-neutralising epitope.

In particular, anti-Tn MAbs KTH1 (IgG1) and KTH2 (IgM) neutralise HIV in vitro infection and syncytium formation, while anti-Tn MAb KTH3 (IgM) cross-reacts with sialosyl-Tn and neutralises HIV infection and syncytium formation. Immunisation of rabbits with Tn-antigen produces a HIV-immuno-neutralising effect, as estimated by the HIV in vitro infection assay.

The conjugate described in Example 2 should have properties similar to native Tn mucin antigens, and should introduce the same humoral (antibody) response in animals and man. By using a peptide sequence from the HIV envelope glycoprotein, it may be assumed that humoral and possible cellular immune responses to the HIV protein will be introduced as well.

What we claim is:

1. A method of inhibiting HIV infection of lymphocytic cells exposed to HIV comprising contacting the lymphocytic cells with an antibody to carbohydrate antigen Tn, wherein said antibody is an amount sufficient to inhibit HIV infection.

2. A method of inhibiting HIV infection of monocytic cells exposed to HIV comprising contacting the monocytic cells with an antibody to carbohydrate antigen Tn, wherein said antibody is an amount sufficient to inhibit HIV infection.

3. The method of claim 1, wherein the antibody is a monoclonal antibody.

4. The method of claim 2, wherein the antibody is a monoclonal antibody.

5. The method of claim 1, wherein the antibody is produced by the hybridoma having all of the characteristics of a hybridoma selected from the group consisting of a hybridoma deposited under accession numbers ECACC 90111401, 90111402, and 90111403.

6. The method of claim 2, wherein the antibody is produced by the hybridoma having all of the characteristics of a hybridoma selected from the group consisting of a hybridoma deposited under accession numbers ECACC 90111401, 90111402, and 90111403.

* * * * *